United States Patent
Auerbach et al.

(10) Patent No.: US 11,430,125 B2
(45) Date of Patent: Aug. 30, 2022

(54) AUTOMATIC DEMARCATION OF ANATOMICAL STRUCTURES

(71) Applicant: Biosense Webster (Israel) Ltd., Yokneam (IL)

(72) Inventors: Shmuel Auerbach, Kerem Maharal (IL); Stanislav Goldberg, Haifa (IL); Oded Baron, Haifa (IL); Iris Segal, Qiryat Motzkin (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 53 days.

(21) Appl. No.: 16/953,446

(22) Filed: Nov. 20, 2020

(65) Prior Publication Data
US 2021/0201493 A1 Jul. 1, 2021

Related U.S. Application Data

(60) Provisional application No. 62/954,194, filed on Dec. 27, 2019.

(51) Int. Cl.
 *G06T 7/10* (2017.01)
 *G06T 7/70* (2017.01)
 (Continued)

(52) U.S. Cl.
 CPC ............ *G06T 7/10* (2017.01); *G06T 7/70* (2017.01); *G06T 19/20* (2013.01); *G16H 30/20* (2018.01);
 (Continued)

(58) Field of Classification Search
 CPC .. G06T 7/10; G06T 7/70; G06T 19/20; G06T 2207/10072; G06T 2207/30048; G06T 2210/41; G16H 30/20; G16H 30/40
 See application file for complete search history.

(56) References Cited

U.S. PATENT DOCUMENTS

| 10,227,063 | B2 * | 3/2019 | Abreu | B60T 7/14 |
| 2004/0114789 | A1 * | 6/2004 | Saha | G06T 7/62 |
| | | | | 382/128 |

(Continued)

FOREIGN PATENT DOCUMENTS

EP    2824639 A2    1/2015

OTHER PUBLICATIONS

European Search Report for corresponding EPA No. 20217185.6 dated Apr. 12, 2021.
(Continued)

*Primary Examiner* — Shefali D Goradia
(74) *Attorney, Agent, or Firm* — Volpe Koenig

(57) ABSTRACT

Methods, apparatuses, systems, and programs are disclosed herein for automatically demarcating segments of an anatomical structure and include providing a processor having a memory, receiving and storing three-dimensional (3D) model data of an anatomical structure of a patient in the memory, generating positional information to orient 3D model data of the anatomical structure, identifying at least one segment of the 3D model data of the anatomical structure based on the positional information, demarcating the at least one identified segment of the 3D model data of the anatomical structure with an identification enhancer that visually distinguishes the at least one identified segment, and providing, for display, the 3D model data of the anatomical structure with the at least one demarcated segment.

19 Claims, 11 Drawing Sheets

(51) Int. Cl.
*G16H 30/20* (2018.01)
*G16H 30/40* (2018.01)
*G06T 19/20* (2011.01)

(52) U.S. Cl.
CPC ... *G16H 30/40* (2018.01); *G06T 2207/10072* (2013.01); *G06T 2207/30048* (2013.01); *G06T 2210/41* (2013.01)

(56) References Cited

U.S. PATENT DOCUMENTS

| | | | | |
|---|---|---|---|---|
| 2004/0242976 | A1* | 12/2004 | Abreu | A61B 5/746 600/315 |
| 2015/0018698 | A1* | 1/2015 | Safran | G06F 17/11 600/508 |

OTHER PUBLICATIONS

Zhang Yonjie et al., "An atlas-based geometry pipeline for cardiac Hermite model construction and diffusion tenso reorientation", Medical Image analysis, vol. 16, No. 6, Aug. 1, 2021, pp. 1130-1141.

Alejandro F. Frangi et al., "Three-Dimensional Modeling for Functional Analysis of Cardiac Images: A Review", IEEE Transactions on Medical Imaging, vol. 20, No. 1, Jan. 1, 2001.

* cited by examiner

AUTOMATIC DEMARCATION OF ANATOMICAL STRUCTURES

CROSS REFERENCE TO RELATED APPLICATION

This application claims the benefit of U.S. Provisional Patent Application Ser. No. 62/954,194, filed on Dec. 27, 2019, which is incorporated by reference as if fully set forth.

FIELD OF INVENTION

The present application provides methods apparatuses, systems, and programs for improving demarcation of anatomical structures for visualization.

BACKGROUND

There is a need to clearly identify segments of anatomical structures of individual patients, such as body organs, for medical treatment and investigation, clinical workflows, and research purposes. Because anatomical structures, such as the chambers of the heart, are typically unique to an individual, variations between corresponding anatomical structures in different individuals has inhibited the use of automated tools to accurately identify the different segments of such structures in a quick and efficient manner.

Conventionally, identification of segments of anatomical structures, such as the left atrium, is manually performed by a medical professional or researcher. However, such manual identification is time consuming, inefficient, and can require the use of special 3D editing software.

Quick and automated identification of segments of anatomical structures can be critical for treating certain conditions. For example, cardiac disorders, such as arrhythmias (e.g., atrial fibrillation), are associated with abnormal conductivity of heart tissue. Procedures for treating cardiac disorders include identifying the origin of the signals causing the arrhythmia and disrupting the conductivity pathway for the erroneous signals. It is possible to interrupt the propagation of the undesirable electric signals by selectively ablating cardiac tissue. For example, electrical pulmonary vein isolation from the left atrium is performed using ablation for treating atrial fibrillation. Pulmonary vein isolation, and many other minimally invasive catheterizations, require real-time visualization and mapping of the left atrium segments.

There exists a need in the art to accurately identify different segments of anatomical structures that are unique to each individual in an automated manner in order to reduce the time and human error involved with such identification.

SUMMARY

Methods, apparatuses, systems, and programs for improving demarcation of anatomical structures for visualization are described herein.

In accordance with one aspect, the subject matter disclosed herein relates to a method for automatically demarcating segments of an anatomical structure and includes providing a processor having a memory, receiving and storing three-dimensional (3D) model data of an anatomical structure of a patient in the memory, generating positional information to orient 3D model data of the anatomical structure, identifying at least one segment of the 3D model data of the anatomical structure based on the positional information, demarcating the at least one identified segment of the 3D model data of the anatomical structure with an identification enhancer that visually distinguishes the at least one identified segment, and providing, for display, the 3D model data of the anatomical structure with the at least one demarcated segment.

In accordance with another aspect, the method further comprises generating a skeleton axis of the 3D model data of the anatomical structure, wherein the positional information to orient the 3D model data of the anatomical structure is generated based on the skeleton axis.

In accordance with another aspect, the anatomical structure is an organ of a patient. In accordance with still another aspect, the anatomical structure is a chamber of a heart of the patient. In accordance with still another aspect, the anatomical structure is a left atrium of a heart of the patient.

In accordance with yet another aspect, the at least one segment comprises at least one pulmonary vein. In accordance with yet another aspect, the skeleton axis comprises at least one branch corresponding to at least one pulmonary vein.

In accordance with yet another aspect, the 3D model data of the anatomical structure comprises a surface mesh.

In accordance with yet another aspect, at least one pulmonary vein is identified by identifying all points on the surface mesh having a similar Euclidian distance from the at least one branch of the skeleton axis to the surface mesh.

In accordance with yet another aspect, the at least one segment comprises at least one of a right superior pulmonary vein, a right inferior pulmonary vein, a left superior pulmonary vein, a left inferior pulmonary vein, and a left atrial appendage. In accordance with yet another aspect, the at least one segment comprises at least one of the following segments of the left atrium: a left atrial appendage, roof, a posterior wall, a septum, an anterior wall, a lateral wall, and a bottom wall.

In accordance with yet another aspect, generating positional information to orient the anatomical structure further comprises accessing a database that stores information from known mappings of similar anatomical structures. In accordance with yet another aspect, generating the positional information comprises identifying at least one of a right side, left side, top side, bottom side, posterior side, and anterior side of the of the 3D model data of the anatomical structure.

In accordance with yet another aspect, identifying at least one segment of the 3D model data of the anatomical structure further comprises generating a graphical cube about the 3D model data of the anatomical structure, the graphical cube comprising a right face, left face, top face, bottom face, posterior face, and anterior face which correspond to the respective right side, left side, top side, bottom side, posterior side, and anterior side of the of the 3D model data of the anatomical structure.

In accordance with yet another aspect, identifying at least one segment of the 3D model data of the anatomical structure further comprises projecting at least one of the right face, left face, top face, bottom face, posterior face, and anterior face of the graphical cube onto a respective right side, left side, top side, bottom side, posterior side, and anterior side of the of the 3D model data of the anatomical structure.

In accordance with yet another aspect, the identification enhancer comprises at least one of color, hatching, shading, and contrast.

In accordance with yet another aspect, a display is provided to display the 3D model data of the anatomical structure with at least one demarcated segment In accordance with yet another aspect, the 3D model data of the anatomical structure of the patient is obtained from an imaging system. In an aspect, the imaging system comprises magnetic resonance imaging (MRI), a computed tomography (CT) scan, x-ray imaging, a rotational angiography, ultrasound imaging, three-dimensional ultrasound imaging, or a three-dimensional mapping.

In accordance with yet another aspect, the subject matter disclosed herein relates to an apparatus for automatically demarcating segments of an anatomical structure and includes a processor comprising a memory. The processor is configured to receive and store three-dimensional (3D) model data of a patient's anatomical structure in the memory, generate a skeleton axis of the 3D model data of the anatomical structure, generate positional information to orient the 3D model data of the anatomical structure based on the skeleton axis, identify at least one segment of the 3D model data of the anatomical structure based on the skeleton axis and the positional information, and demarcate the at least one identified segment of the 3D model data of the anatomical structure with an identification enhancer that visually distinguishes the at least one identified segment. The apparatus further includes a display in communication with the processor to display the 3D model data of the anatomical structure with the at least one demarcated segment.

In accordance with yet another aspect, the subject matter disclosed herein relates to a system for automatically demarcating segments of an anatomical structure, and includes a processor comprising a memory and a display in communication with the processor. The processor is configured to receive and store three-dimensional (3D) model data of a patient's anatomical structure in the memory, generate a skeleton axis of the 3D model data of the anatomical structure, generate positional information to orient the 3D model data of the anatomical structure based on the skeleton axis, identify at least one segment of the 3D model data of the anatomical structure based on the skeleton axis and the positional information, demarcate the at least one identified segment of the 3D model data of the anatomical structure with an identification enhancer that visually distinguishes the at least one identified segment, and communicate with the display to display the 3D model data of the anatomical structure with the at least one demarcated segment on the display.

In accordance with yet another aspect, the subject matter disclosed herein relates to a non-transitory computer readable recording medium storing program instructions for automatically demarcating segments of three-dimensional (3D) model data of a patient's anatomical structure by causing a computer to execute the steps of receiving and storing the three-dimensional (3D) model data of the patient's anatomical structure of a patient in the memory, generating a skeleton axis of the 3D model data of the patient's anatomical structure, generating positional information to orient 3D model data of the patient's anatomical structure based on the skeleton axis, identifying at least one segment of the 3D model data of the patient's anatomical structure based on the skeleton axis and the positional information, demarcating the at least one identified segment of the 3D model data of the patient's anatomical structure with an identification enhancer that visually distinguishes the at least one identified segment, and providing, for display, the 3D model data of the patient's anatomical structure with the at least one demarcated segment.

BRIEF DESCRIPTION OF THE DRAWINGS

A more detailed understanding can be had from the following description, given by way of example in conjunction with the accompanying drawings wherein.

DETAILED DESCRIPTION OF THE PREFERRED EMBODIMENTS

A method, system, and program is provided that enables automatic demarcation of segments of anatomical structures, such as body organs, in unique patients for efficient and accurate visualization of such structures.

In an exemplary embodiment, model data of a patient's anatomical structure is automatically segmented and visualized on a display. The model data is preferably three-dimensional model data of a left atrium (LA) of an individual patient's heart. While automatic segmentation of the left atrium is described herein as an exemplary embodiment, one of ordinary skill in the art will readily understand that the method, system, and program according to the disclosed subject matter herein can be applied to automatically segment and display other organs or anatomical structures and/or portions thereof.

According to exemplary embodiments disclosed herein, a system is provided that receives model data of a patient's anatomical structure. The model data can be obtained by an imaging system such as by magnetic resonance imaging (MRI), computed tomography (CT) scanning, x-ray imaging, rotational angiography, ultrasound imaging, three-dimensional ultrasound imaging, three-dimensional mapping, or any other means for two-dimensional imaging, three-dimensional imaging, and combinations of two-dimensional and three-dimensional imaging. The system preferably includes a processing device with a communication device that receives the model data of the patient's anatomical structure. Upon receiving the model data, the processing device preferably orients the anatomical structure, for example, by generating a skeleton axis of the anatomical structure, identifies readily recognizable structures, such as major veins, and incrementally enhances the segments of the anatomical structure with an identification enhancer. The identification enhancer preferably differentiates the individual segments and can be based on, without limitation, a color, hatching, shading, contrast, etc. The identification enhancer is preferably overlaid on the model data and displayed on a display.

Figure 1:
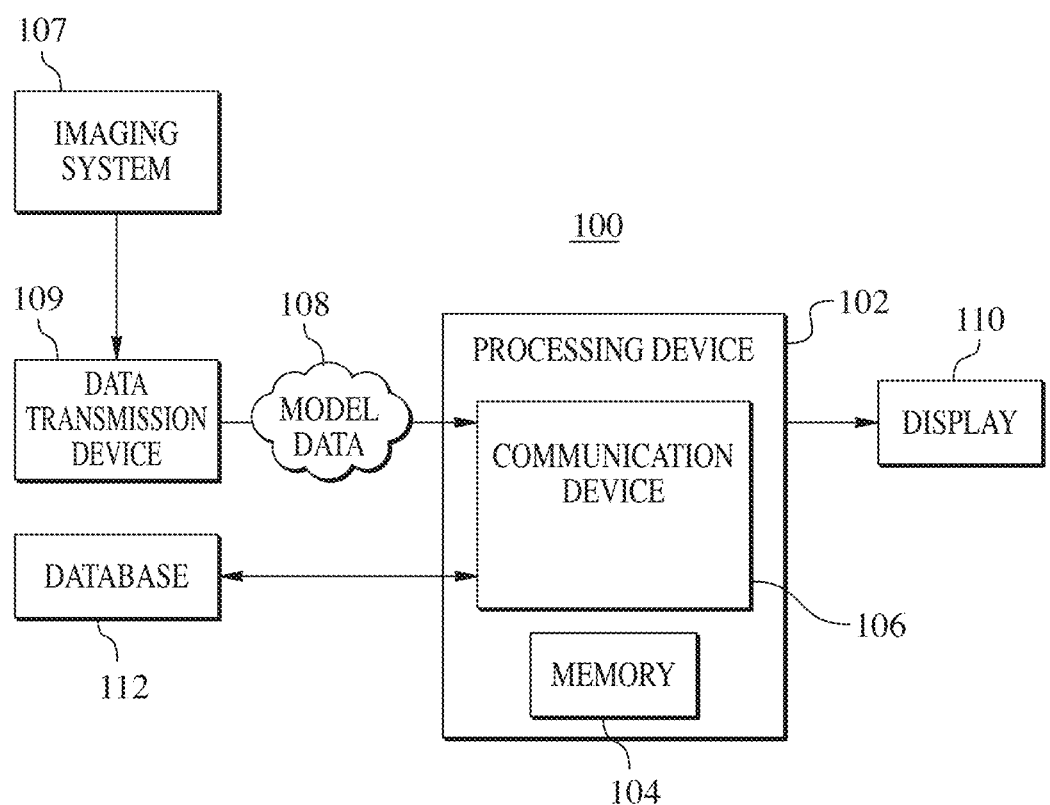
FIG. 1 is a schematic representation of an apparatus and system for generating and displaying model data of an anatomical structure with segments automatically demarcated in accordance with the present invention.

Referring to FIG. 1, an exemplary system 100 that enables automatic demarcation of segments of an individual patient's anatomical structures is provided. The system 100 preferably includes a processing device 102. Processing device 102 may control other components of the system 100 according to the embodiments described herein. According to an exemplary embodiment, the processing device 102 may include a memory 104. Memory 104 may comprise any suitable volatile and/or non-volatile memory, such as random-access memory (RAM), a register, cache memory, semiconductor memory devices, magnetic media such as internal hard disks and removable disks, magneto-optical media, and optical media such as CD-ROM disks, and digital versatile disks (DVDs). Processing device 102 preferably executes a software program and/or program stored in hardware to perform the functions required by the system 100. Processing device 102 may execute a software program stored in the memory 104. The software may be downloaded to the processing device 102 in electronic form, over a network, or may be provided on tangible media, such as optical, magnetic, or other nonvolatile memory media.

According to an exemplary embodiment, processing device 102 may be implemented in a general-purpose computer, a special purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements the methods described herein.

According to an exemplary embodiment, processing device 102 preferably includes a communication device 106 configured to receive model data 108 of a patient's anatomical structure, such as a three-dimensional model data of an organ or portion of an organ obtained by an imaging system 107, such as by magnetic resonance imaging (MRI), computed tomography (CT) scanning, x-ray imaging, rotational angiography, ultrasound imaging, three-dimensional ultrasound imaging, three-dimensional mapping, or any other means for two-dimensional imaging, three-dimensional imaging, and combinations of two-dimensional and three-dimensional imaging. The communication device 106 preferably receives the model data 108 from a data transmission device 109 that can be integrated with the imaging system 107 or separate from, but in communication with, the imaging system 107. The communication device 106 may have a wired or wireless connection with the data transmission device 109 or may receive the model data 108 over the Internet or a network. The network may be any network or system generally known in the art such as an intranet, a local area network (LAN), a wide area network (WAN), a metropolitan area network (MAN), a direct connection or series of connections, a cellular telephone network, or any other network or medium capable of facilitating communication with the processing device 102. The network may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite, or any other wireless connection methodology generally known in the art.

According to an exemplary embodiment, the model data 108 may be electronic data derived from imaging a patient's anatomical structure. In an exemplary embodiment, the model data 108 is three-dimensional (3D) model data derived from an image of a patient's organ, such as a left atrium of the heart. Upon receipt of the model data 108 by the processing device, the model data 108 may be stored in the memory 104.

According to an exemplary embodiment, processing device 102 may be coupled to a display 110 to produce a visual display of the model data 108. The display 110 may be integrated with the processing device 102 or external to the processing device 102.

According to an exemplary embodiment, the processing device 102 may transmit or receive information from a database 112. The database 112 may be a storage device (auxiliary storage device) storing various types of information determined in advance. In an exemplary embodiment, the database 112 can be integral with the processing device 102, such as an internally fixed storage medium (e.g., a built-in memory, etc.) or a removable storage medium (e.g., a removable card-type memory, etc.). However, the configuration of the database 112 is not limited to such forms. In another exemplary embodiment, the database 112 may be configured by an external storage device in an independent form. In this case that the database 112 is external to the processing device 102, and the processing device 102 includes a communication unit, such as communication device 106, to enable transmission and receiving of various types of information to/from the database 112.

According to an exemplary embodiment, the database 112 stores information such as location information, orientation information, or structural information of an anatomical structure. For example, the database 112 may store information relating to the orientation of an organ, such as the left atrium of the heart. The database 112, may also store information to identify and locate known structures within an organ, such as, without limitation, veins, chambers, walls, arteries, muscles, tendons, linings, layers, etc., that can be used to map out segments of a patient's organ, such as the left atrium. In an exemplary embodiment, the processing device 102 can utilize information from the database 112 to identify readily recognizable structures, such as pulmonary veins in an image of a patient's left atrium. The location of the veins can be used to identify other segments of an organ, such as the left atrium of the heart, as will be explained in greater detail hereinafter.

In an exemplary embodiment, the processing device 102 preferably orients the anatomical structure, for example, by generating a surface mesh of the anatomical structure in the model data 108, such as a polygon mesh, and more preferably, such as a triangular mesh, of the anatomical structure 108 according to known methods for graphical modeling. Alternatively, the model data 108 of the anatomical structure received from the data transmission device 109 may already have a surface mesh generated thereon.

In an exemplary embodiment, the processing device 102 preferably generates a skeleton axis or topographical skeleton of the anatomical structure by known methods and algorithms for creating a skeleton axis, such as, and without limitation, by shrinking or collapsing the surface mesh of the model data 108 of the anatomical structure to generate a medial axis or main axis along the medial portion of the structure and any extending branch portions, such as, without limitation, veins, arteries, appendages, etc. One of ordinary skill in the art will recognize that other known methods or algorithms for generating a skeleton axis can be utilized within the scope of the present application.

In an exemplary embodiment, the processing device 102 preferably orients the anatomical structure in the model data 108 by identifying three dimensional sides, such as, and without limitation, the posterior, anterior, top, bottom, right and left sides of the anatomical structure. In a non-limiting example, the processing device can identify the posterior, anterior, top, bottom, right and left sides of the model data 108 of a patient's anatomical structure by receiving data that identifies the position of the patient's body or organ relative to the imaging system 109 when the model data 108 is generated for the patient. Alternatively, the processing device 102 can identify the posterior, anterior, top, bottom, right and left sides of the model data 108 of a patient's anatomical structure by communicating with the database 112 to compare the skeleton axis of the model data 108 with a database containing known anatomical mappings for similar anatomical structures.

In an exemplary embodiment, the processing device 102 relies on the skeleton axis and the orientation of the anatomical structure to automatically identify segments of the anatomical structure, and incrementally enhance the identified segments of the anatomical structure with an identification enhancer, as will be explained in detail hereinafter. The identification enhancer is preferably overlaid or superimposed on the model data 108 of the anatomical structure and displayed on the display 110 to visually differentiate the individual segments of the anatomical structure.

Figure 2:
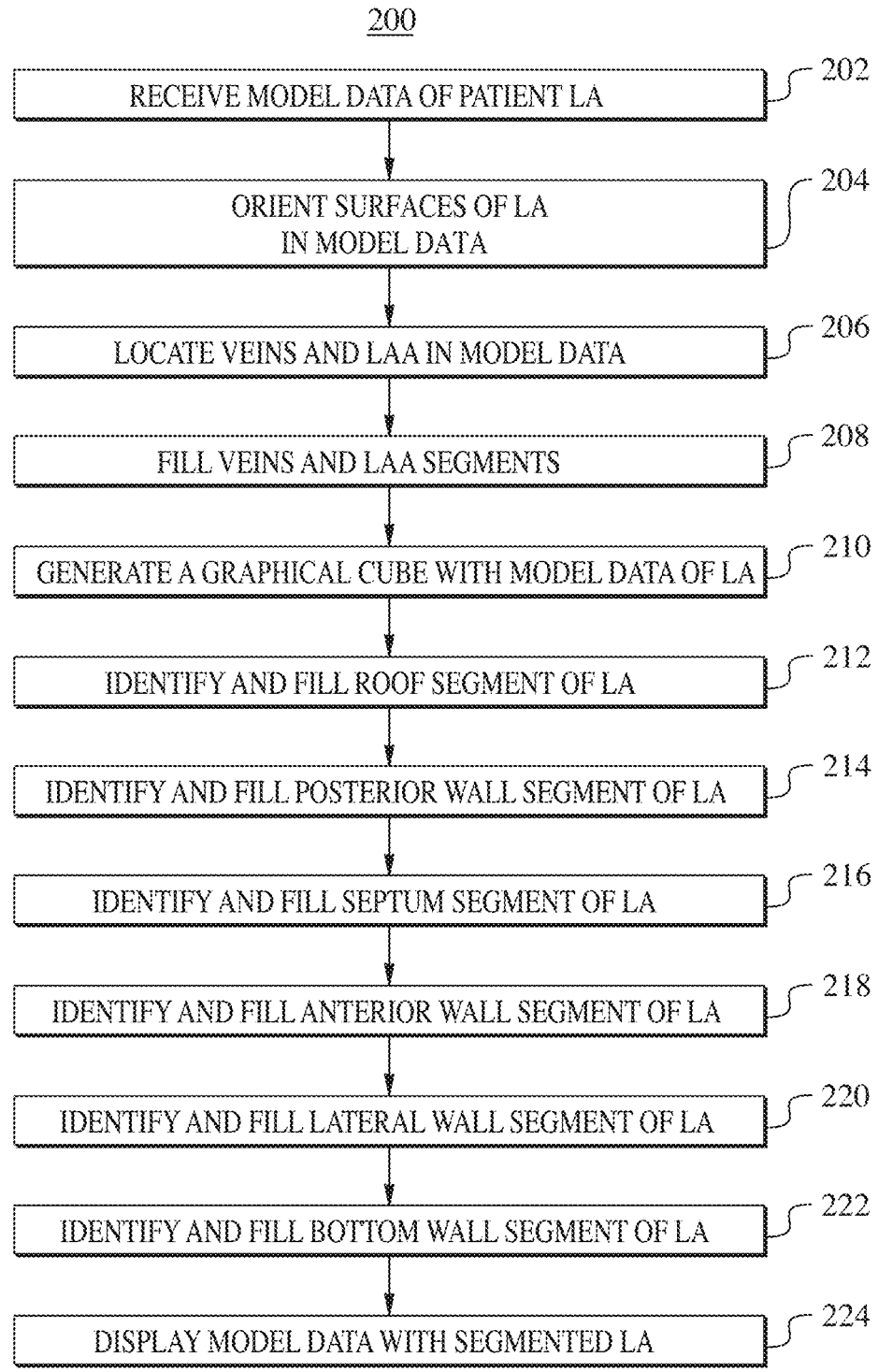
FIG. 2 is a flowchart illustrating an exemplary embodiment for generating and displaying model data of a left atrium with its segments automatically demarcated in accordance with the present invention.

FIG. 2 is an exemplary embodiment of a process 200 for generating and displaying an anatomical structure with segments automatically demarcated utilizing the system 100 described herein. In particular, FIG. 2 describes an exemplary process 200 for generating and displaying three-dimensional model data of a left atrium (LA) 300 (FIG. 3) of the heart with segments automatically demarcated utilizing the system 100 described herein. More particularly, FIG. 2 describes an exemplary process 200 for generating and displaying a left atrium of the heart with at least the following segments automatically demarcated: right superior pulmonary vein (RSPV), right inferior pulmonary vein (RIPV), left superior pulmonary vein (LSPV), left inferior pulmonary vein (LIPV), left atrial appendage (LAA), roof, posterior wall, septum, anterior wall, lateral wall, and bottom wall.

Figure 3:
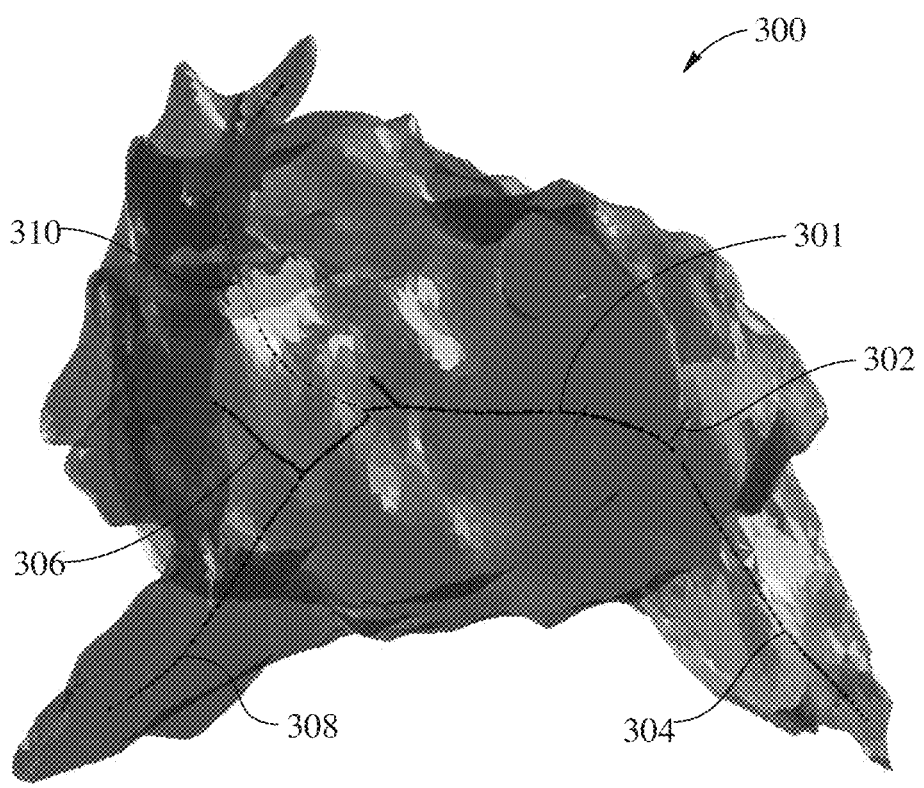
FIG. 3 is an exemplary embodiment of a posterior view of three-dimensional model data of a left atrium with a skeleton axis displayed in accordance with the present invention.
Figure 4A:
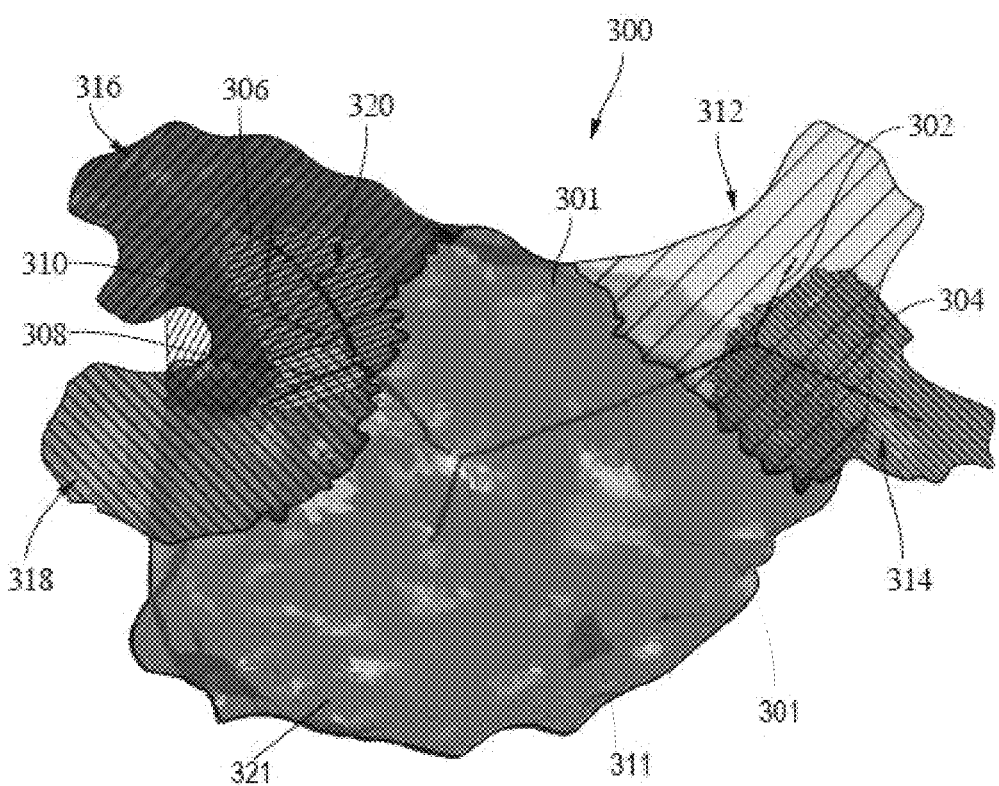
FIG. 4A is an exemplary embodiment of another posterior view of the three-dimensional model data of the left atrium which is slightly rotated relative to FIG. 3 to show more of the bottom wall and showing the pulmonary veins and left atrial appendage demarcated with an identification enhancer in accordance with the present invention.
Figure 4B:
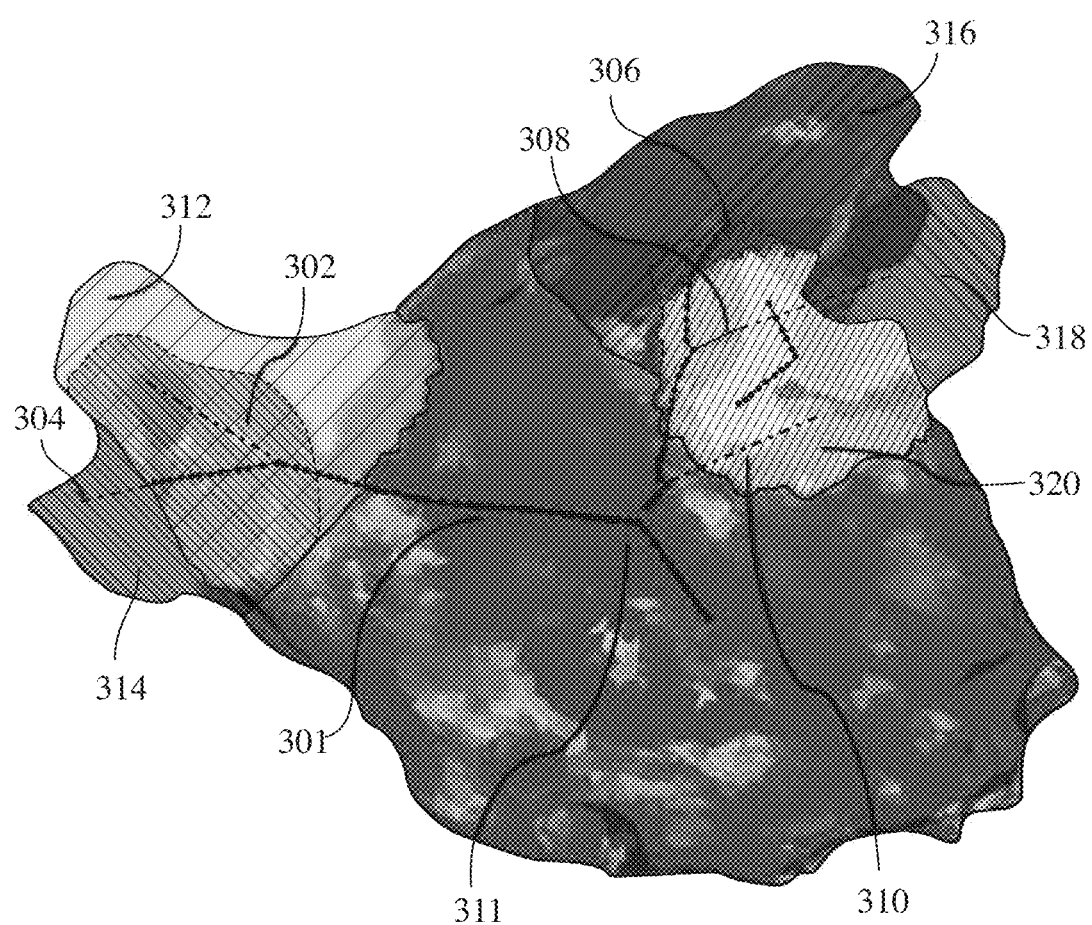
FIG. 4B is an exemplary embodiment of an anterior view of the three-dimensional model data of the left atrium showing the pulmonary veins and left atrial appendage demarcated with an identification enhancer in accordance with the present invention.
Figure 5:
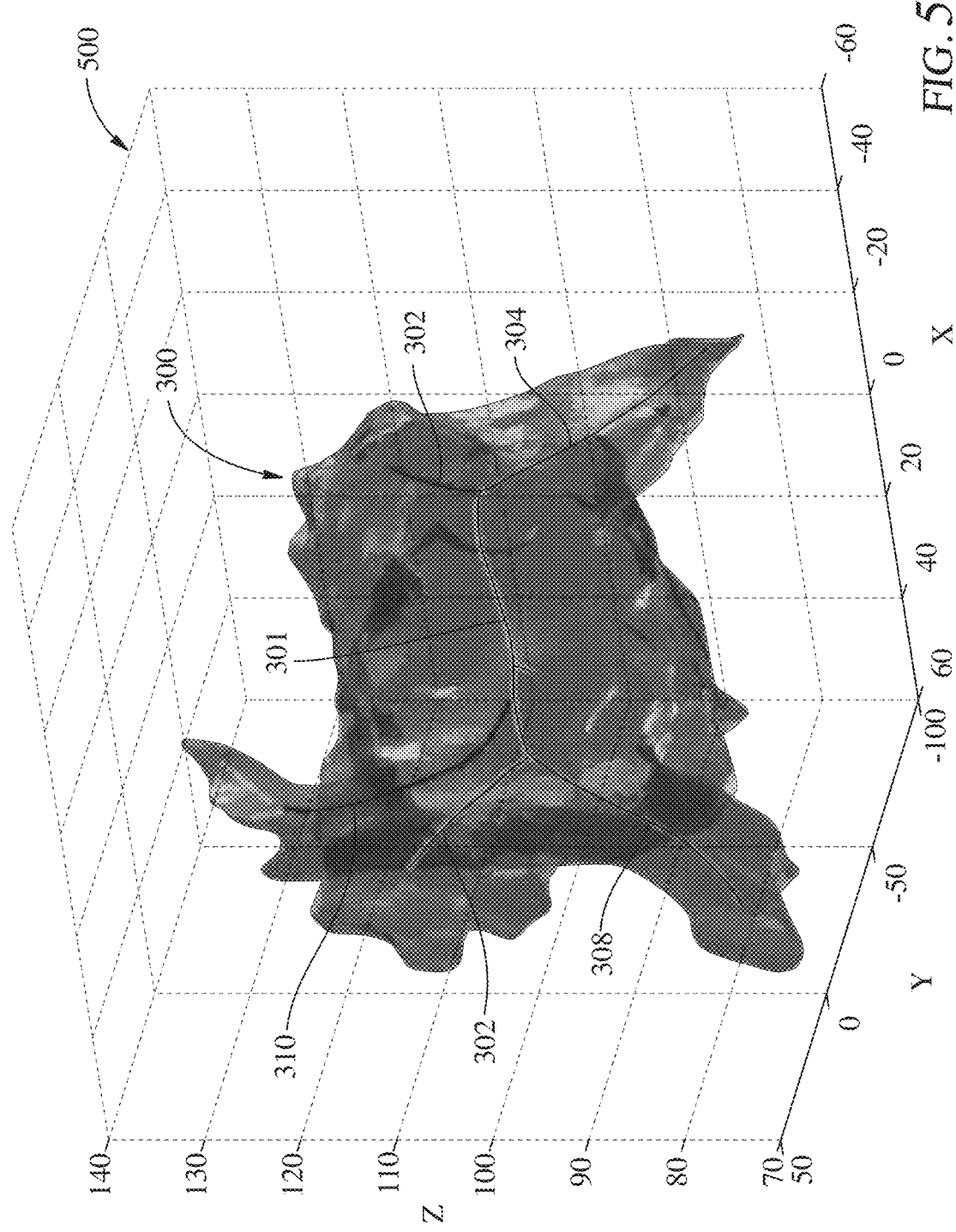
FIG. 5 is an exemplary embodiment of a posterior view of the three-dimensional model data of the left atrium within a graphical cube according to an exemplary embodiment of the invention showing with the skeleton axis displayed.
Figure 6:
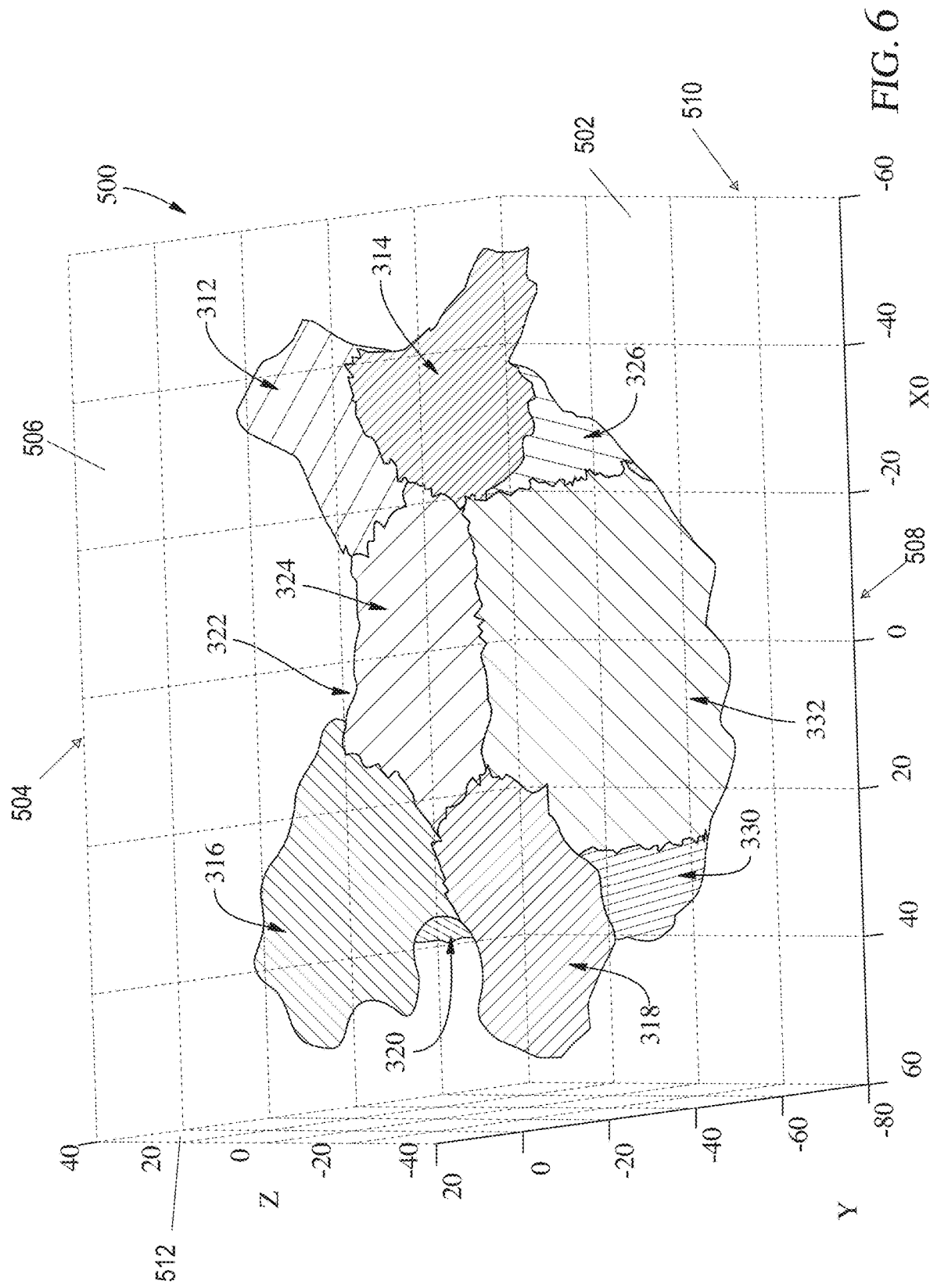
FIG. 6 is an exemplary embodiment of a posterior side view of the three-dimensional model data of the left atrium within a graphical cube according to an exemplary embodiment of the invention showing the atrial segments demarcated with an identification enhancer.

At step 202 of FIG. 2, the processing device 102 receives model data of a patient's left atrium 300 via the communication device 106. As described above, the model data of the patient's left atrium 300 can be obtained by an imaging system, such as by magnetic resonance imaging (MRI), computed tomography (CT) scan, x-ray imaging, rotational angiography, ultrasound imaging, three-dimensional ultrasound imaging, three-dimensional mapping, or any other means for two-dimensional and three-dimensional imaging. FIGS. 3 and 4A illustrate exemplary embodiments of a posterior view of three-dimensional (3D) model data of the left atrium 300 of the patient's heart, and FIG. 4B illustrates an exemplary embodiment of an anterior view of the 3D model data of the left atrium 300. The 3D model data of the left atrium 300 can be displayed on display 110. In an exemplary embodiment, the 3D model data of the left atrium 300 can be generated with a surface mesh, such as a polygon mesh, and more preferably, with a triangular mesh.

At step 204 of FIG. 2, the processing device 102 preferably orients the 3D model data of the left atrium 300. For example, and without limitation the processing device 102 preferably generates a skeleton axis of the 3D model data of the left atrium 300 and orients the 3D model data of the left atrium 300. FIGS. 3, 4A, and 4B illustrate an exemplary embodiment of a skeleton axis displayed on the 3D model data of the left atrium 300 which includes a main axis 301 and five (5) branch axes comprising: a right superior pulmonary vein (RSPV) axis 302, a right inferior pulmonary vein (RIPV) axis 304, a left superior pulmonary vein (LSPV) axis 306, a left inferior pulmonary vein (LIPV) axis 308, and a left atrial appendage (LAA) axis 310. The processing device 102 then preferably identifies three-dimensional orientation information of the left atrium in the 3D model data of the left atrium 300. For example, and without limitation, the processing device 102 can establish right, left, top, bottom, posterior, and anterior sides or surfaces of the 3D model of the left atrium 300 based on the known position of the patient's heart relative to the imaging system 107 when the model data 301 is generated. Alternatively, the processing device 102 can identify the posterior, anterior, top, bottom, right and left sides of the 3D model data of the patient's left atrium 300 by communicating with the database 112 to compare the skeleton axis (301, 302, 304, 306, 308, 310) of the 3D model data of the left atrium 300 with information from the database 112 containing known mapping information for the left atrium.

At step 206 of FIG. 2, the processing device 102 preferably locates well-recognized structures in the 3D model data of the left atrium 300 based on the skeleton axis 301, 302, 304, 306, 308, 310 and the orientation information. In an exemplary embodiment, the well-recognized structures include, without limitation, major veins, such as, the right superior pulmonary vein (RSPV) 312, right inferior pulmonary vein (RIPV) 314, left superior pulmonary vein (LSPV) 316, left inferior pulmonary vein (LIPV) 318, and the left atrial appendage (LAA) 320 as shown in FIGS. 4A and 4B.

In an exemplary embodiment as shown in FIG. 4A, the pulmonary veins 312, 314, 316, 318 and LAA 320 can be identified by orienting the 3D model data of the left atrium 300 in a posterior view, and identifying the two major branches of the skeleton axis 302, 304 at the right side to be the RSPV 312 and RIPV 314, wherein the upper branch, or RSPV axis 302, of the skeleton axis is used to identify the RSPV 312 and the lower branch, or RIPV axis 304, of the skeleton axis is used to identify the RIPV 314. Similarly, the three major branches of the skeleton axis 306, 308, 310 at the left side of the 3D model data of the left atrium 300 are used to identify the LSPV 316, LIPV 318, and LAA 320, wherein the upper branch, or LSPV axis 306, of the skeleton axis is used to identify the LSPV 316, the lower branch, or LIPV axis 308, of the skeleton axis is used to identify the LIPV 318, and the middle branch, or LAA axis 310, of the skeleton axis is used to identify the LAA 320. While the posterior view of the 3D model data of the left atrium 300 is used in the foregoing, non-limiting example to describe the process of identifying the pulmonary veins and LAA, one of ordinary skill in the art will recognize that the 3D model data of the left atrium 300 can be oriented in any view to perform this identification. For example, FIG. 4B illustrates an exemplary embodiment of an anterior view of the 3D model data of the left atrium 300 showing the identified pulmonary veins 312, 314, 316, 318 and LAA 320.

In another exemplary embodiment, the processing device 102 can orient the 3D model data of the left atrium 300 without generating a skeleton axis of the 3D model data of the left atrium 300 as described in steps 204 and 206 of FIG. 2. Instead, the processing device 102 can identify the RSPV 312, RIPV 314, LSPV 316, LIPV 318, and the left atrial appendage LAA 320 by communicating with the database 112 to compare the 3D model data of the left atrium 300 with information from the database 112 containing known mapping information for the left atrium.

At step 208 of FIG. 2, the processing device 102 preferably establishes where the pulmonary veins 312, 314, 316, 318, and LAA 320 integrate with the body 321 of the left atrium and demarcates the pulmonary veins 312, 314, 316, 318, and LAA 320 in the 3D model data of the left atrium with an identification enhancer as shown in FIGS. 4A and 4B. According to an exemplary embodiment, in order to demarcate the pulmonary veins 312, 314, 316, 318 and the LAA 320, the processing device 102 preferably identifies branch axis pairs of the skeleton axis having a common branch point from the main axis 301, such as: RSPV axis 302—RIPV axis 304; LSPV axis 306—LIPV axis 308; and LSPV axis 306—LAA axis 310. For each identified branch axis pair, the processing device 102 identifies all points $P_a$ on the surface mesh of the 3D model data of the left atrium 300 having a similar Euclidian distance from the respective branch axis pair to the surface mesh. The points $P_a$ on the surface mesh for each of the pulmonary veins 312, 314, 316, 318 and LAA 320 that are closest to a center point 311 of the main axis 301 define a boundary $P_b$ between the body 321 of the left atrium and the respective pulmonary veins 312, 314, 316, 318 and LAA 320. The boundary $P_b$ preferably coincides with the common branch point between the branch axis pairs and the main axis 301. The points $P_a$ on the surface mesh of the 3D model data of the left atrium 300 are used to demarcate the pulmonary veins 312, 314, 316, 318 and LAA 320 within the respective boundaries $P_b$. Although the process for identifying the pulmonary veins 312, 314, 316, 318 and the LAA 320 described above is slated to begin by identifying "branch axis pairs" of the skeleton axis, one of ordinary skill in the art will understand that the process can also be performed for each branch axis 302, 304, 306, 308, 310 individually.

In a preferred embodiment, the processing device 102 preferably superimposes an identification enhancer on each of the identified pulmonary veins 312, 314, 316, 318, and LAA 320 in the 3D model data to differentiate them for demarcation and visual recognition. The identification enhancer can be, without limitation, a color, hatching, shading, contrast, or any other means to visually distinguish structures. The identification enhancer is preferably superimposed on the 3D model data of the left atrium 300 and displayed on the display 110. FIGS. 4A and 4B illustrates exemplary embodiments in which an identification enhancer is superimposed on segments of the 3D model data of the left atrium, including the RSPV 312, RIPV 314, LSPV 316, LIPV 318, and LAA 320. As described herein, the identification enhancer visually distinguishes the pulmonary veins 312, 314, 316, 318 and LAA 320 from one another.

At step 210 of FIG. 2, the processing device 102 preferably generates a graphical cube 500 about the 3D model data of the left atrium 300 to assist with the process of segment demarcation as shown in FIGS. 5-12. The graphical cube 500 includes posterior 502, anterior 504, top 506, bottom 508, right 510, and left 512 faces. The process of segment demarcation is further described in steps 212 through 222 of FIG. 2.

In an embodiment, the graphical cube is preferably generated by creating a rectangle for the top face 506 in which the rectangle's vertices are positioned adjacent the RSPV 312, RIPV 314, LSPV 316, and LIPV 318. The top face 506 is pulled down to form a 3D graphical cube 500 in which the bottom face 508 is adjacent the lowest point of the 3D model data of the left atrium 300 (see FIG. 6).

Figure 13:
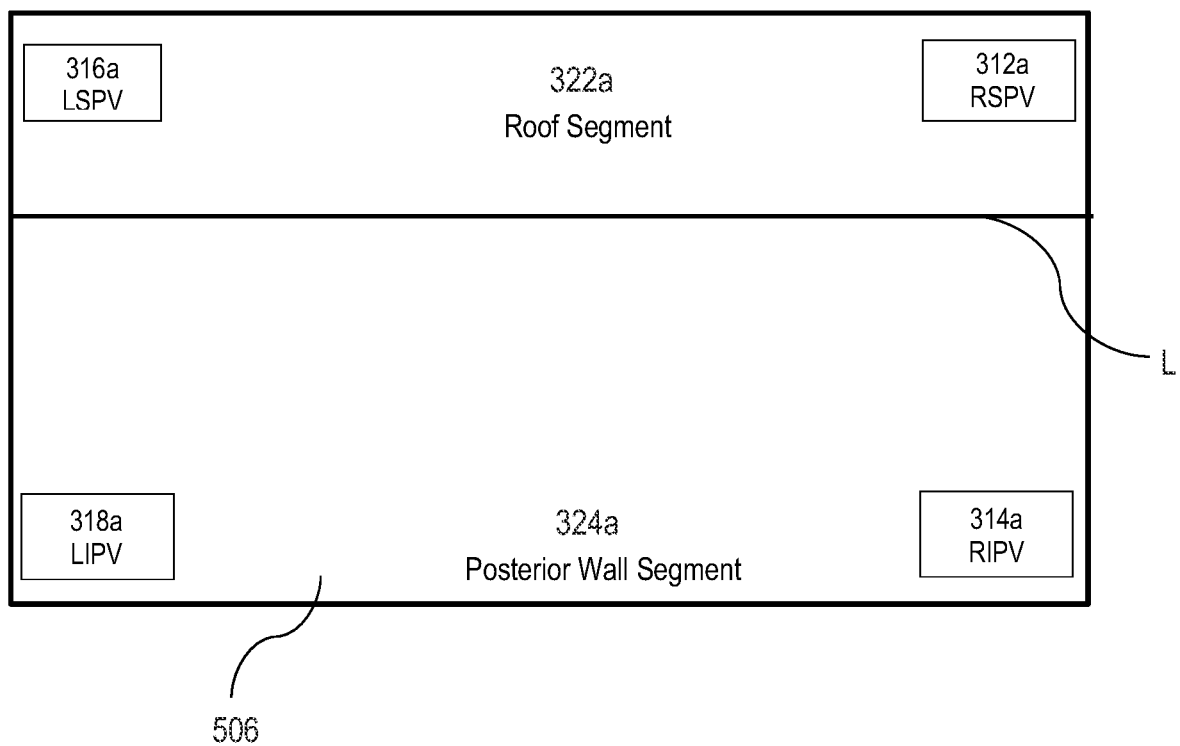
FIG. 13 is a plan view of a top face of the graphical cube showing an exemplary division of the surface area of the top face in accordance with the present invention.

At step 212 of FIG. 2, the processing device 102 identifies the roof segment 322 of the left atrium in the 3D model data of the left atrium 300. The processing device 102 preferably identifies the roof segment 322 by orienting a surface in the surface mesh of the 3D model data of the lower atrium 300 between the boundaries $P_b$ for each of the RSPV 312, RIPV 314, LSPV 316, and LIPV 318, respectively, adjacent a top face 506 of the graphical cube 500. In an exemplary embodiment, as shown in FIG. 13, the relative locations of the RSPV 312, RIPV 314, LSPV 316, LIPV 318 preferably form corresponding corner points 312a, 314a, 316a, 318a in the top face 506 of the graphical cube 500. In an exemplary embodiment, the processing device divides the top face 506 by generating line L parallel to an edge formed by corners 312a-316a and an edge formed by corners 314a-318a. Line L is preferably generated in a manner to divide a surface area representing the roof segment 322a from a surface area representing the posterior wall segment 324a in the top face 506 of the graphical cube 500 based on predetermined surface areas from known 3D mappings of roof segments relative to the posterior walls. In an exemplary embodiment, the processing device 102 can access the database 112 to obtain the predetermined surface areas. In an exemplary embodiment, the top face 506 of the graphical cube is divided by Line L such that the surface area representing the roof segment 322a is smaller than the surface area representing the posterior wall 324a. In an embodiment, the surface area representing the roof segment 322a is approximately 20%-30% of the surface area of the top face 506 and the surface area representing the posterior wall 324a is approximately 70%-80% of the surface area of the top face 506. One of ordinary skill in the art will recognize that the foregoing percentages of the surface area of the top face 506 can be modified based on the particular anatomical structure or organ in the subject model data 1098. In an exemplary embodiment, the smaller surface area 322a of the top face 506 of the graphical cube 500 is projected onto the surface mesh of the 3D model of the lower atrium 300 to define the roof segment 322. Upon identification, the roof segment 322 is preferably denoted with an identification enhancer, such as a color, hatching, shading, contrast, etc., for visual identification of the roof segment 322 on the display 110 as shown in FIGS. 6, 7, 8, and 10.

At step 214 of FIG. 2, the processing device 102 identifies the posterior wall segment 324 of the left atrium in the 3D model data of the left atrium 300. The processing device 102 preferably identifies the posterior wall segment 324 by identifying a segment of the left atrium adjacent the roof segment 322 and between the boundaries $P_b$ for the RSPV 312, RIPV 314, LSPV 316, and LIPV 318 using the process described above with respect to identification of the roof segment 322. In particular, the larger surface area 324a of the top face 506 of the graphical cube 500 is projected onto the surface mesh of the 3D model of the lower atrium 300 to define the posterior wall segment 324. Upon identification, the posterior wall segment 324 is preferably denoted with an identification enhancer for visual identification of the posterior wall segment 324 on the display 110 as shown in FIGS. 6-8, 10, and 12.

At step 216 of FIG. 2, the processing device 102 identifies the septum segment 326 of the left atrium in the 3D model data of the left atrium 300. The processing device 102 preferably identifies the septum segment 326 by projecting the right face 510 of the graphical cube 500 onto the surface mesh of the 3D model of the lower atrium 300 and identifying a segment of the left atrium adjacent the RSPV 312, RIPV 314 as the septum segment 326. Upon identification, the septum segment 326 is preferably denoted with an identification enhancer for visual identification of the septum segment 326 on the display 110 as shown in FIGS. 6-12.

Figure 7:
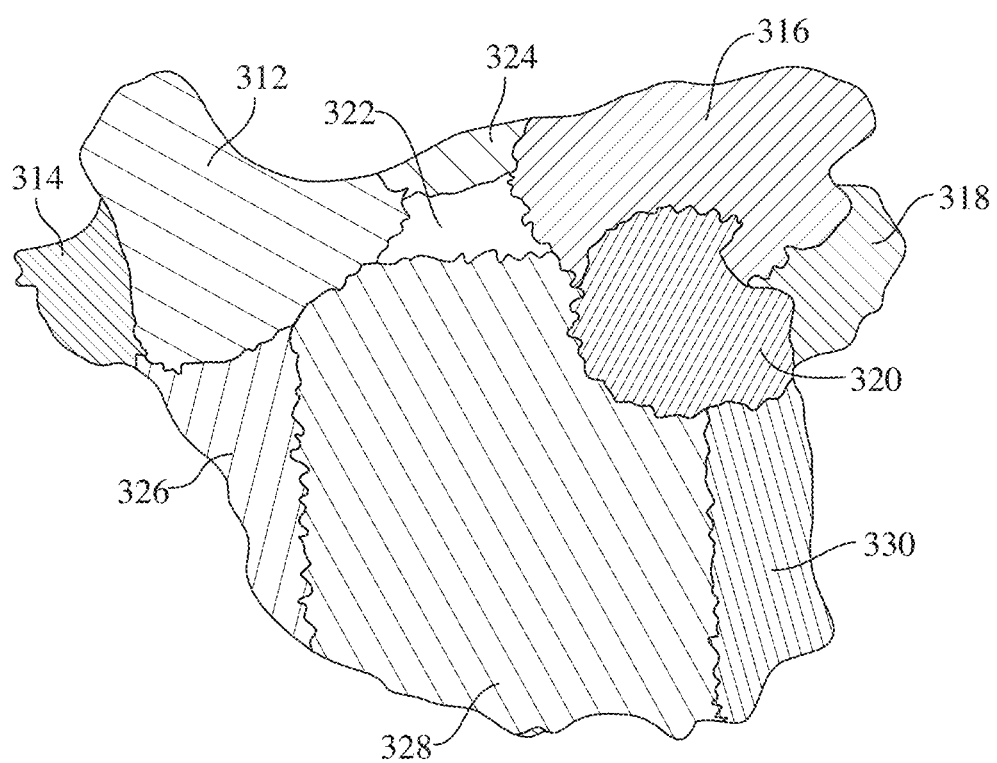
FIG. 7 is an anterior side view of the three-dimensional model data of the left atrium of FIG. 6 without the graphical cube displayed in accordance with the present invention.
Figure 8:
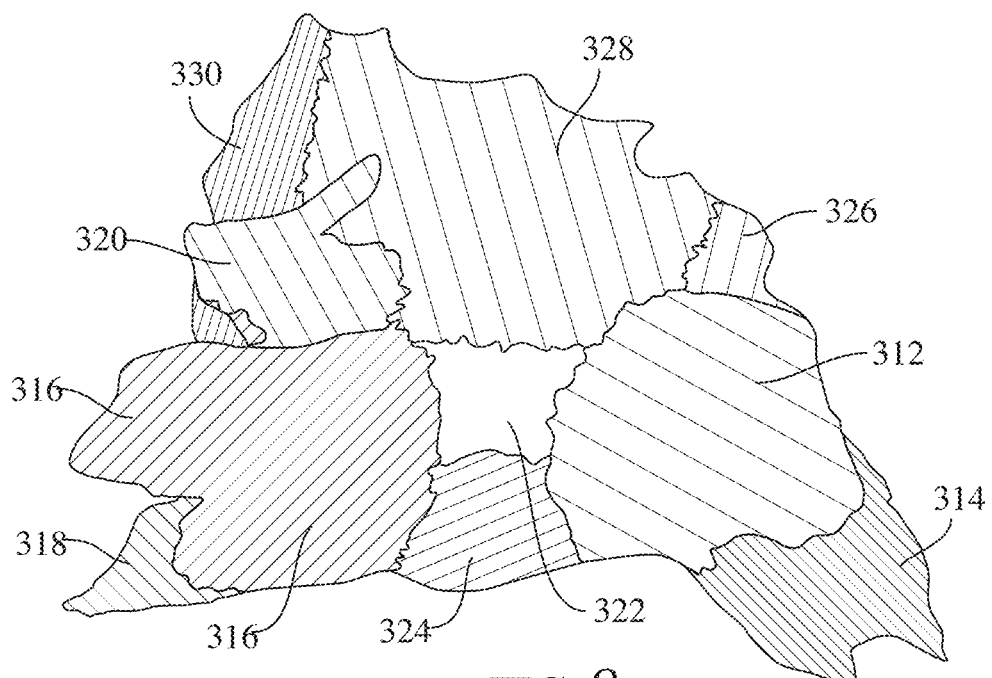
FIG. 8 is a top side view of the three-dimensional model data of the left atrium of FIG. 6 in accordance with the present invention.
Figure 9:
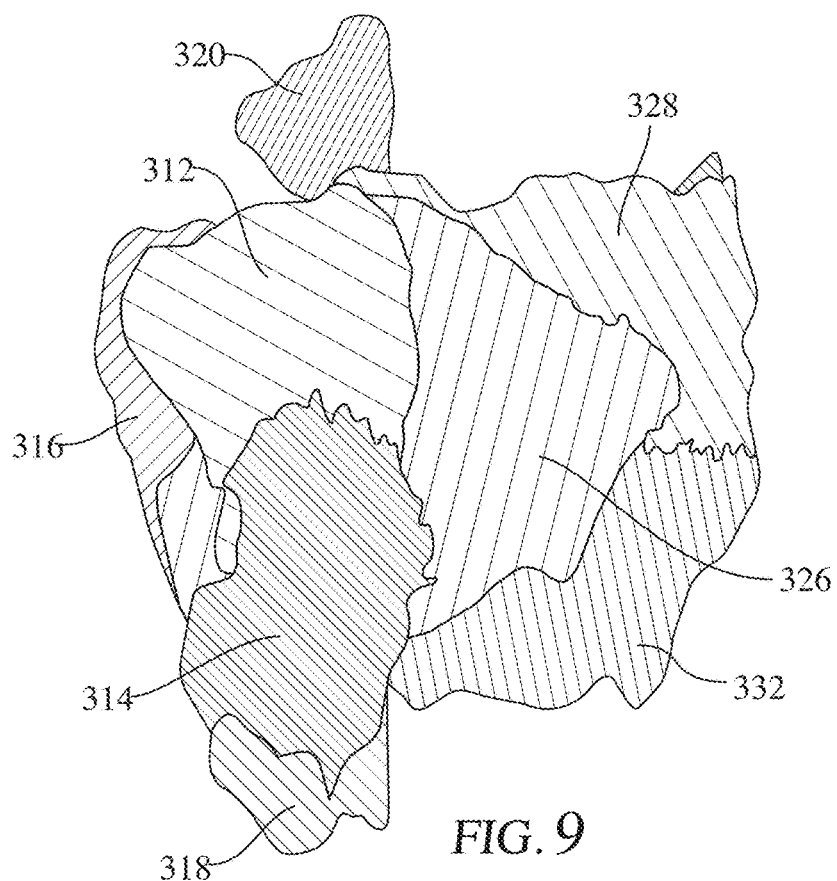
FIG. 9 is a right side view of the three-dimensional model data of the left atrium of FIG. 6 in accordance with the present invention.
Figure 10:
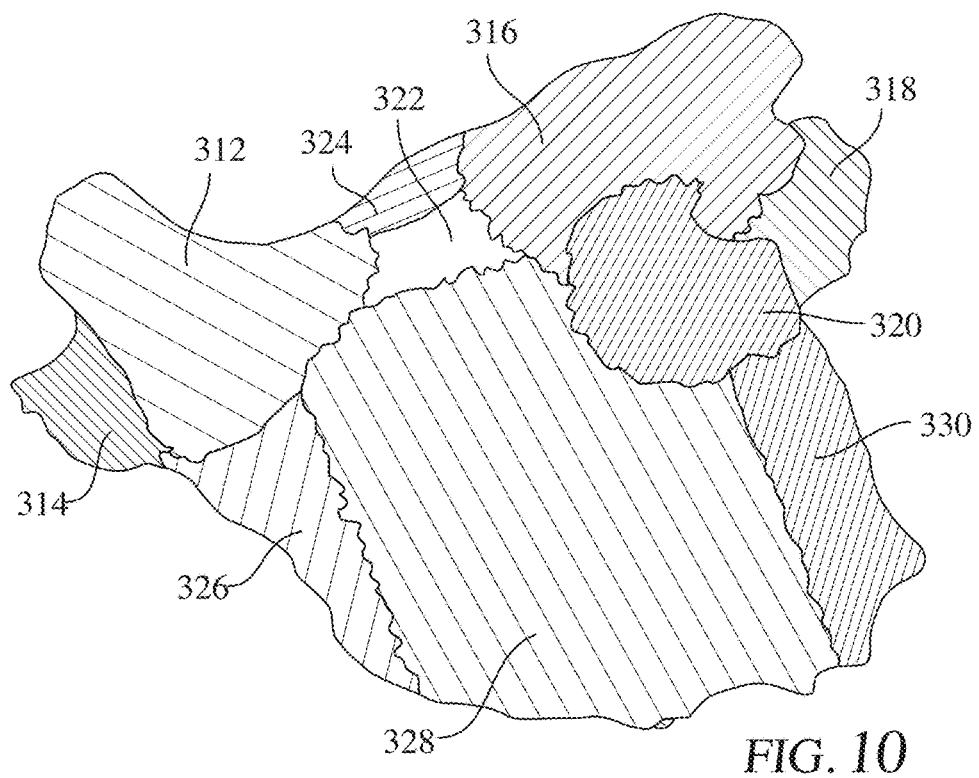
FIG. 10 is another anterior side view of the three-dimensional model data of the left atrium of FIG. 6 in accordance with the present invention.
Figure 11:
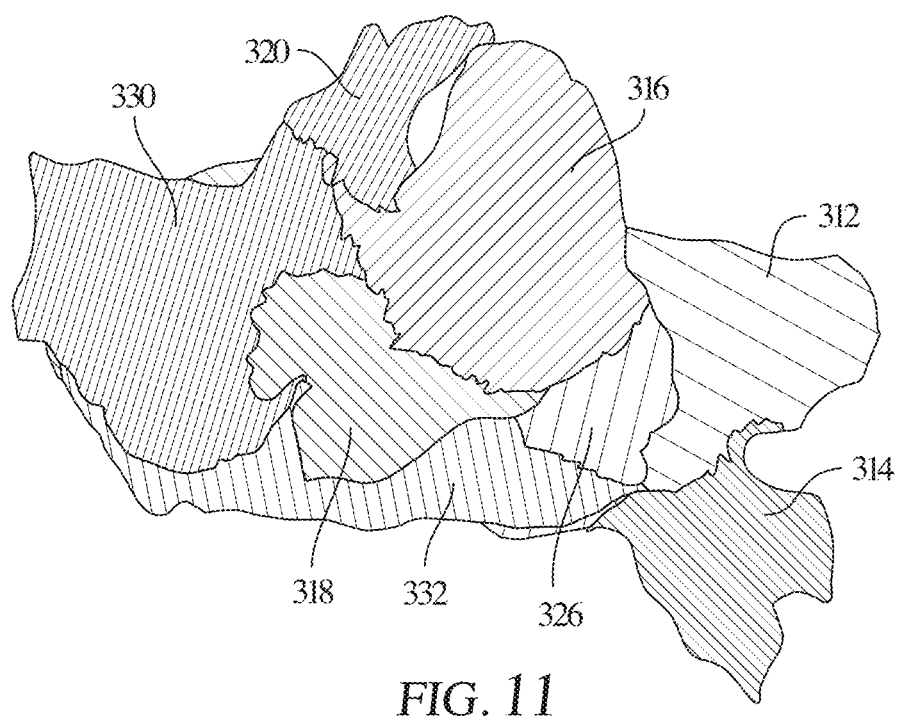
FIG. 11 is a left side view of the three-dimensional model data of the left atrium of FIG. 6 in accordance with the present invention.
Figure 12:
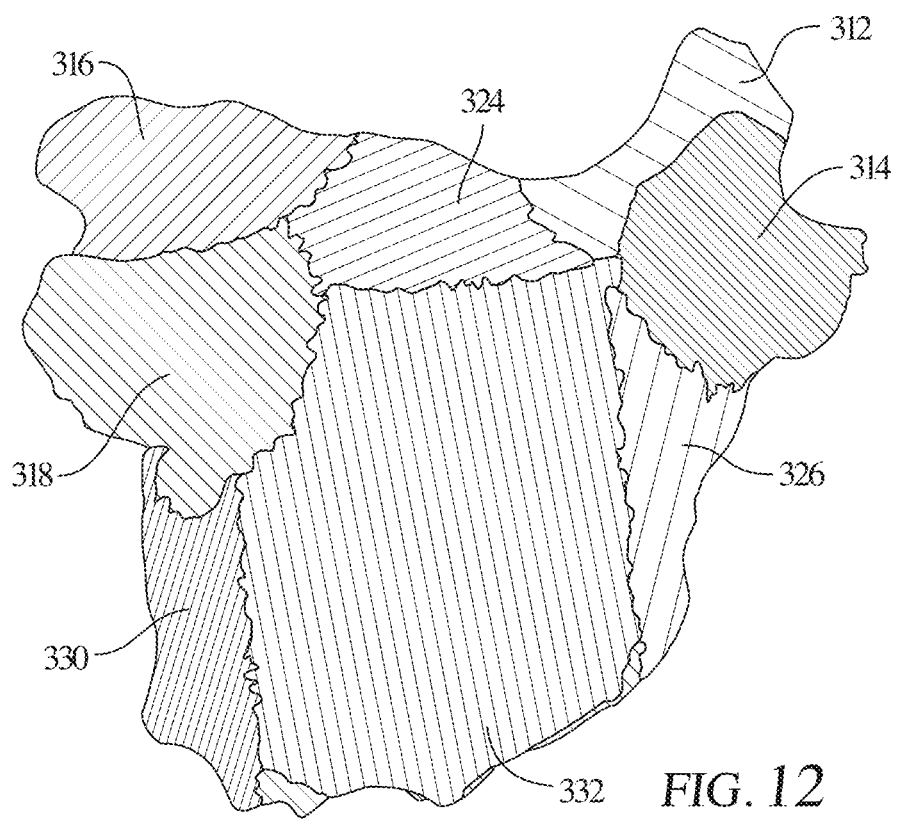
FIG. 12 is a bottom side view of the three-dimensional model data of the left atrium of FIG. 6 in accordance with the present invention.

At step 218 of FIG. 2, the processing device 102 identifies the anterior wall segment 328 of the left atrium in the 3D model data of the left atrium 300. The processing device 102 preferably identifies the anterior wall segment 328 by projecting the anterior face 504 of the graphical cube 500 onto the surface mesh of the 3D model of the lower atrium 300 and identifying a segment of the left atrium adjacent the RSPV 312, LAA 320, roof segment 322, and septum segment 326 as the anterior wall segment. Upon identification, the anterior wall segment 328 is preferably denoted with an identification enhancer for visual identification of the anterior wall segment 328 on the display 110 as shown in FIGS. 7, 9, and 10.

At step 220 of FIG. 2, the processing device 102 identifies the lateral wall segment 330 of the left atrium in the 3D model data of the left atrium 300. The processing device 102 preferably identifies the lateral wall segment 330 by projecting the left face 512 of the graphical cube 500 onto the surface mesh of the 3D model of the lower atrium 300 and identifying a segment of the left atrium adjacent the LSPV 316, LIPV 318, and LAA 320 and the anterior wall segment 328 as the lateral wall segment 330. Upon identification, the lateral wall segment 330 is preferably denoted with an identification enhancer for visual identification of the lateral wall segment 330 on the display 110 as shown in FIGS. 6-8, 10, and 12.

At step 222 of FIG. 2, the processing device 102 identifies the bottom wall segment 332 of the left atrium in the 3D model data of the left atrium 300. The processing device 102 preferably identifies the bottom wall segment 332 by projecting the bottom face 508 of the graphical cube 500 onto the surface mesh of the 3D model of the lower atrium 300 and identifying a segment of the left atrium adjacent the RIPV 316, LIPV 318, LAA 320, posterior wall segment 324, anterior wall segment 328, septum segment 326, and lateral wall segment 330 as the bottom wall segment 332. Upon identification, the bottom wall segment 332 is preferably denoted with an identification enhancer for visual identification of the bottom wall segment 332 on the display 110.

After step 222, the processing device expands the boundaries of each segment until contact is made with other segments to fill the 3D model data of the left atrium 300 with identification enhancers to visually distinguish the demarcated segments.

At step 224 of FIG. 2, the segmented 3D model data of the left atrium 300 is preferably displayed on the display 110 showing different identification enhancers to visually distinguish the demarcated segments. One of ordinary skill in the art will readily understand that different identification enhancers, such as, for example, different colors, can be used to visually distinguish the various identified structures.

According to an exemplary embodiment, each, or any of steps 204-224 of process 200 can be incrementally displayed on the display 110 during each respective step of the process 200.

One of ordinary skill in the art would readily understand that steps 204-224 of process 200 can be incrementally performed in any preferred order, and that certain steps of process 200 can be eliminated or additional process steps can be added to identify other segments of the left atrium not specifically mentioned herein.

While FIGS. 2-13 and the disclosure herein relate an exemplary process 200 for generating and displaying a left atrium (LA) of the heart with segments automatically demarcated utilizing the system 100 described herein, one of ordinary skill in the art will readily understand that the disclosed process can be applied to automatically segment and display other organs or anatomical structures.

The subject matter disclosed herein for automatic demarcation of an anatomical structure reduces the time involved to segment anatomical structures as compared to conventional techniques which require manual segmentation, and it provides more accurate and predictable data by minimizing any human error.

It should be understood that many variations are possible based on the disclosure herein. Although features and elements are described above in particular combinations, each feature or element can be used alone without the other features and elements or in various combinations with or without other features and elements. Similarly, although process steps are described above in a particular order, the steps can be performed in other desirable orders.

The methods, processes and/or flow charts provided herein can be implemented in a computer program, software, or firmware incorporated in a non-transitory computer-readable storage medium for execution by a general-purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

Certain terminology is used in the description herein for convenience only and is not limiting. The words "right," "left," "top," "bottom," "front," and "back" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Further exemplary embodiments herein may be formed by supplementing an embodiment with one or more element from any one or more other embodiment herein, and/or substituting one or more element from one embodiment with one or more element from one or more other embodiment herein.

It is understood, therefore, that the disclosed subject matter is not limited to the particular embodiments disclosed, but is intended to cover all modifications which are within the spirit and scope of the invention as defined by the appended claims; the above description; and/or shown in the attached drawings.

What is claimed is:

1. A method for automatically demarcating segments of an anatomical structure, comprising:
   providing a processor having a memory;
   receiving and storing three-dimensional (3D) model data of an anatomical structure of a patient in the memory;
   generating positional information to orient the 3D model data of the anatomical structure by identifying at least one of a plurality of sides of the 3D model data of the anatomical structure;
   identifying at least one segment of the 3D model data of the anatomical structure based on the positional information, the identifying including generating a 3D graphical shape about the 3D model data of the anatomical structure, the 3D graphical shape comprising a plurality of faces, one of the plurality of faces respectively corresponding to the at least one of the plurality of sides of the 3D model data of the anatomical structure;
   demarcating the at least one identified segment of the 3D model data of the anatomical structure with an identification enhancer that visually distinguishes the at least one identified segment; and
   providing, for display, the 3D model data of the anatomical structure with the at least one demarcated segment.

2. The method of claim 1, further comprising:
   generating a skeleton axis of the 3D model data of the anatomical structure,
   wherein the positional information to orient the 3D model data of the anatomical structure is generated based on the skeleton axis.

3. The method of claim 1, wherein the anatomical structure is a left atrium of a heart of the patient, and the at least one segment comprises at least one pulmonary vein.

4. The method claim 3, wherein
   the skeleton axis comprises at least one branch corresponding to the at least one pulmonary vein,
   the 3D model data of the anatomical structure comprises a surface mesh, and
   the at least one pulmonary vein is identified by identifying all points on the surface mesh having a similar Euclidian distance from the at least one branch of the skeleton axis to the surface mesh.

5. The method of claim 1, wherein the at least one segment comprises at least one of a right superior pulmonary vein, a right inferior pulmonary vein, a left superior pulmonary vein, a left inferior pulmonary vein, and a left atrial appendage, a roof, a posterior wall, a septum, an anterior wall, a lateral wall, and a bottom wall.

6. The method of claim 1, wherein generating positional information to orient the anatomical structure further comprises accessing a database that stores information from known mappings of similar anatomical structures, and
   identifying at least one of a plurality of sides of the 3D model data of the anatomical structure comprises identifying at least one of a right side, left side, top side, bottom side, posterior side, and anterior side of the of the 3D model data of the anatomical structure.

7. The method of claim 6, wherein generating the 3D graphical shape further comprises generating a graphical cube about the 3D model data of the anatomical structure, the graphical cube comprising a right face, left face, top face, bottom face, posterior face, and anterior face which correspond to the respective right side, left side, top side, bottom side, posterior side, and anterior side of the of the 3D model data of the anatomical structure.

8. The method of claim 7, wherein identifying at least one segment of the 3D model data of the anatomical structure further comprises projecting at least one of the right face, left face, top face, bottom face, posterior face, and anterior face of the graphical cube onto the respective right side, left side, top side, bottom side, posterior side, and anterior side of the of the 3D model data of the anatomical structure.

9. The method of claim 1, wherein the identification enhancer comprises at least one of color, hatching, shading, and contrast.

10. The method of claim 1, wherein the 3D model data of the anatomical structure is obtained from an imaging system.

11. A system for automatically demarcating segments of an anatomical structure, comprising:
   a processor comprising a memory; and
   a display in communication with the processor;
   wherein the processor is configured to:
      receive and store three-dimensional (3D) model data of a patient's anatomical structure in the memory;
      generate a skeleton axis of the 3D model data of the anatomical structure;
      generate positional information to orient the 3D model data of the anatomical structure based on the skeleton axis by identifying at least one of a plurality of sides of the 3D model data of the anatomical structure;
      identify at least one segment of the 3D model data of the anatomical structure based on the skeleton axis and the positional information by generating a 3D graphical shape about the 3D model data of the anatomical structure, the 3D graphical shape comprising a plurality of faces, one of the plurality of faces respectively corresponding to the at least one of the plurality of sides of the 3D model data of the anatomical structure;
      demarcate the at least one identified segment of the 3D model data of the anatomical structure with an identification enhancer that visually distinguishes the at least one identified segment; and
      communicate with the display to display the 3D model data of the anatomical structure with the at least one demarcated segment on the display.

12. The system of claim 11, wherein the anatomical structure is a left atrium of a heart of the patient, and the at least one segment comprises at least one of a right superior pulmonary vein, a right inferior pulmonary vein, a left superior pulmonary vein, a left inferior pulmonary vein, and a left atrial appendage, a roof, a posterior wall, a septum, an anterior wall, a lateral wall, and a bottom wall.

13. The system of claim 11, further comprising a database in communication with the processor that stores information from known mappings of similar anatomical structures.

14. The system of claim 11, wherein:
the skeleton axis comprises at least one branch corresponding to at least one pulmonary vein;
the 3D model data of the anatomical structure comprises a surface mesh; and
the at least one pulmonary vein is identified by identifying all points on the surface mesh having a similar Euclidian distance from the at least one branch of the skeleton axis to the surface mesh.

15. The system of claim 11, wherein
identifying at least one of a plurality of sides of the 3D model data of the anatomical structure comprises identifying at least one of a right side, left side, top side, bottom side, posterior side, and anterior side of the of the 3D model data of the anatomical structure; and
generating the 3D graphical shape further comprises generating a graphical cube about the 3D model data of the anatomical structure, the graphical cube comprising a right face, left face, top face, bottom face, posterior face, and anterior face which correspond to the respective right side, left side, top side, bottom side, posterior side, and anterior side of the of the 3D model data of the anatomical structure.

16. A non-transitory computer readable recording medium storing program instructions for automatically demarcating segments of three-dimensional (3D) model data of a patient's anatomical structure by causing a computer to execute the steps of:
receiving and storing the three-dimensional (3D) model data of the patient's anatomical structure of a patient;
generating a skeleton axis of the 3D model data of the patient's anatomical structure;
generating positional information to orient 3D model data of the patient's anatomical structure based on the skeleton axis by identifying at least one of a right side, left side, top side, bottom side, posterior side, and anterior side of the of the 3D model data of the patient's anatomical structure;
identifying at least one segment of the 3D model data of the patient's anatomical structure based on the skeleton axis and the positional information by generating a graphical cube about the 3D model data of the patient's anatomical structure, the graphical cube comprising a right face, left face, top face, bottom face, posterior face, and anterior face which correspond to the respective right side, left side, top side, bottom side, posterior side, and anterior side of the of the 3D model data of the patient's anatomical structure;
demarcating the at least one identified segment of the 3D model data of the patient's anatomical structure with an identification enhancer that visually distinguishes the at least one identified segment; and
providing, for display, the 3D model data of the patient's anatomical structure with the at least one demarcated segment.

17. The non-transitory computer readable recording medium of claim 16, wherein the anatomical structure is a left atrium of a heart of the patient, and the at least one segment comprises at least one of a right superior pulmonary vein, a right inferior pulmonary vein, a left superior pulmonary vein, a left inferior pulmonary vein, and a left atrial appendage, a roof, a posterior wall, a septum, an anterior wall, a lateral wall, and a bottom wall.

18. The non-transitory computer readable recording medium of claim 16, further comprising a database in communication with the computer that stores information from known mappings of similar anatomical structures.

19. The non-transitory computer readable recording medium of claim 16, wherein:
the skeleton axis comprises at least one branch corresponding to at least one pulmonary vein;
the 3D model data of the patient's anatomical structure comprises a surface mesh; and
the at least one pulmonary vein is identified by identifying all points on the surface mesh having a similar Euclidian distance from the at least one branch of the skeleton axis to the surface mesh.

\* \* \* \* \*

UNITED STATES PATENT AND TRADEMARK OFFICE
CERTIFICATE OF CORRECTION

PATENT NO. : 11,430,125 B2
APPLICATION NO. : 16/953446
DATED : August 30, 2022
INVENTOR(S) : Shmuel Auerbach et al.

It is certified that error appears in the above-identified patent and that said Letters Patent is hereby corrected as shown below:

On the Title Page
Item (72), under "Inventors", in Column 1, Line 4, delete "Qiryat Motzkin" and insert -- Kiryat Motzkin --, therefor.

In the Specification
In Column 2, Line 44, delete "of the of the" and insert -- of the --, therefor at each occurrence throughout the specification.
In Column 2, Line 67, delete "segment" and insert -- segment. --, therefor.
In Column 7, Lines 24-25, delete "anatomical structure 108" and insert -- anatomical structure --, therefor.
In Column 7, Line 50, delete "imaging system 109" and insert -- imaging system 107 --, therefor.
In Column 8, Line 55, delete "model data 301" and insert -- model data 108 --, therefor.
In Column 10, Line 17, delete "illustrate" and insert -- illustrates --, therefor.
In Column 10, Line 43, delete "lower atrium 300" and insert -- left atrium 300 --, therefor.
In Column 10, Line 63, delete "Line L" and insert -- line L --, therefor.
In Column 10, Line 65, delete "posterior wall 324a." and insert -- posterior wall segment 324a. --, therefor.
In Column 11, Line 1, delete "posterior wall 324a" and insert -- posterior wall segment 324a --, therefor.
In Column 11, Line 6, delete "model data 1098." and insert -- model data 108. --, therefor.
In Column 11, Line 7, delete "smaller surface area 322a" and insert -- roof segment 322a --, therefor.
In Column 11, Line 9, delete "lower atrium 300" and insert -- left atrium 300 --, therefor.
In Column 11, Line 23, delete "larger surface area 324a" and insert -- posterior wall segment 324a --, therefor.
In Column 11, Line 25, delete "lower atrium 300" and insert -- left atrium 300 --, therefor.
In Column 11, Line 36, delete "lower atrium 300" and insert -- left atrium 300 --, therefor.
In Column 11, Line 47, delete "lower atrium 300" and insert -- left atrium 300 --, therefor.
In Column 11, Line 60, delete "lower atrium 300" and insert -- left atrium 300 --, therefor.
In Column 12, Line 6, delete "lower atrium 300" and insert -- left atrium 300 --, therefor.
In Column 12, Line 8, delete "RIPV 316," and insert -- RIPV 314, --, therefor.

Signed and Sealed this
Twelfth Day of September, 2023

Katherine Kelly Vidal
*Director of the United States Patent and Trademark Office*

In the Claims

In Column 13, Line 59, in Claim 4, delete "method" and insert -- method of --, therefor.